US00PP33468P2

(12) United States Plant Patent
Wilhoite et al.

(10) Patent No.: US PP33,468 P2
(45) Date of Patent: Sep. 7, 2021

(54) ***HOSTA* PLANT NAMED 'SISTER ACT'**

(50) Latin Name: ***Hosta* hybrid**
Varietal Denomination: Sister Act

(71) Applicants: Chris Wilhoite, Indianapolis, IN (US); Cynthia Miller, Indianapolis, IN (US)

(72) Inventors: Chris Wilhoite, Indianapolis, IN (US); Cynthia Miller, Indianapolis, IN (US)

( * ) Notice: Subject to any disclaimer, the term of this patent is extended or adjusted under 35 U.S.C. 154(b) by 0 days.

(21) Appl. No.: 17/300,068

(22) Filed: Mar. 1, 2021

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./263.1, 353
See application file for complete search history.

*Primary Examiner* — Susan McCormick Ewoldt
*Assistant Examiner* — Karen M Redden

(57) ABSTRACT

A new and distinct *Hosta* plant named 'Sister Act' of low spreading mound of dense variegated foliage with wide green margins, chartreuse centers and jutting sections of the margins shooting into the center and from the center shooting into the margins. The flowers are near white, with greenish bracts below, on scapes just above the foliage. 'Sister Act' is useful in the landscape as a specimen or en masse.

2 Drawing Sheets

Botanical classification: *Hosta* hybrid.
Variety denomination: 'Sister Act'.

STATEMENT REGARDING PRIOR DISCLOSURES UNDER 37 CFR 1.77(B)(6)

*Hosta* 'Sister Act' was first introduced by the inventor as a brief non-enabling description and photograph on the website maintained by Walters Gardens, Inc. on Feb. 1, 2020. The first sale of the new plant was by Walters Gardens, Inc. on Mar. 2, 2020. Walters Gardens, Inc. obtained the new plant and all information about the new plant from me. No plants of *Hosta* 'Sister Act' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Sister Act' hereinafter also referred to as the new plant or by the cultivar name, 'Sister Act'. *Hosta* 'Sister Act' was sport mutation found in May of 2007 by the inventors, Chris Wilhoite and Cynthia Miller, on plants of *Hosta* 'Step Sister' (not patented) in a commercial perennial nursery in Indianapolis, Ind.

The new plant has been asexually propagated by division at the same nursery since 2010 and also by careful shoot tip plant tissue culture with the resultant asexually propagated plants having retained all the same traits as the original plant. *Hosta* 'Sister Act' is stable and reproduces true to type in successive generations of asexual reproduction.

There are over 7,300 registered and established *Hosta* cultivars accepted and recorded with The American *Hosta* Society, which is the International Cultivar Registration Authority for the genus *Hosta*. The new plant has not yet been registered with the International Cultivar Registration Authority. Several of these other registered and established cultivars have green leaf margins with chartreuse variegated leaf centers. The most similar *Hosta* cultivars known to the applicant are 'Beyond Glory' U.S. Plant Pat. No. 28,784, 'Brother Stefan' (not patented), 'California Gold Rush' (not patented), 'First Dance' (not patented), 'St Paul' (not patented), 'Captain Kirk' (not patented) and 'Heat Wave' (not patented), 'Paradigm' (not patented).

'Beyond Glory' has a less compact habit, the foliage is more rounded with more sharply acute apices and the flowers are medium lavender and more clustered in the terminal portion of taller scapes. 'Brother Stefan' has a taller and broader habit, the foliage is more dimpled and corrugated and the flowering is much closer to the top of the foliage. 'California Gold Rush' has leaves that are slightly more rounded, the floral bracts are more lavender tinted, the leaf margin is narrower and lighter green and the jutting between the margin and center is less pronounced. 'First Dance' has a taller, broader, more arching habit with larger and more pointed foliage and larger scapes with light lavender flowers. 'St Paul' has a taller more upright habit, the leaves are more glaucous above, the leaf margins are broader and the flowers are a light lavender. 'Captain Kirk' has less compact habit, the foliage is more rounded, the leaf center becomes a lighter yellowish color and the margin is narrower. 'Heat Wave' is less compact in habit, the leaves are more glaucous bluish-green on the margin, and the flowers are pale lavender. 'Paradigm' is taller in habit, the foliage is larger, more rounded and more dimpled, and the flowers open wider and have a light lavender band on the inside of the tepals. Both 'Heat Wave' and 'St Paul' have similar leaf thickness (between top and bottom of a leaf) while the other comparison varieties referenced above have thinner leaves.

The sport parent, 'Step Sister', has leaves with similar color variegation in the margin and center but the margins are narrower and the habit of the plant is broader and bigger.

Other *Hosta* cultivars may have variegated ovate leaf blades with bluish-green margins and chartreuse to yellow centers, or other individual traits similar to 'Sister Act' but the new plant differs from the above listed cultivars and all other *Hostas* known to the applicant, by the combination of the following traits.

1. Habit is a low spreading mound of dense foliage;
2. Leaves are medium-sized, lightly glaucous, ovate, thick textured, with acute apices and cordate base;
3. Leaves have a wide green margin and a chartreuse center with some dimpling and corrugation throughout;
4. The transition between the margin and the center of the leaves consists of many jutting sections of the margins shooting into the center and the center shooting into the margins;
5. Flowers are near white, faintly blushed with light lavender and densely arranged on slightly arching scapes with the first flowers beginning to open just above the foliage;
6. Flowers are subtended by lanceolate, short, greenish, floral bracts.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color. The drawings show 'Sister Act' plant in various growing conditions.

DETAILED BOTANICAL DESCRIPTION

Figure 1:
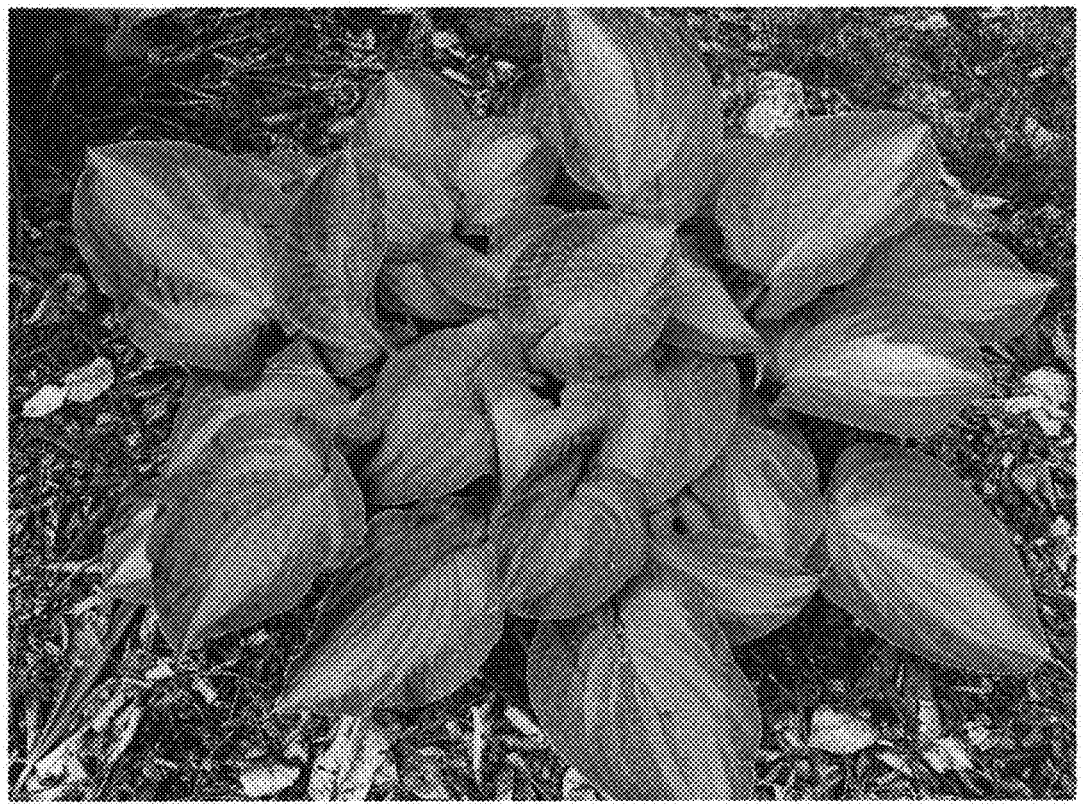
FIG. 1 shows a mature ten-year-old plant viewed from above in a display garden at a nursery in Indianapolis, Ind.
Figure 2:
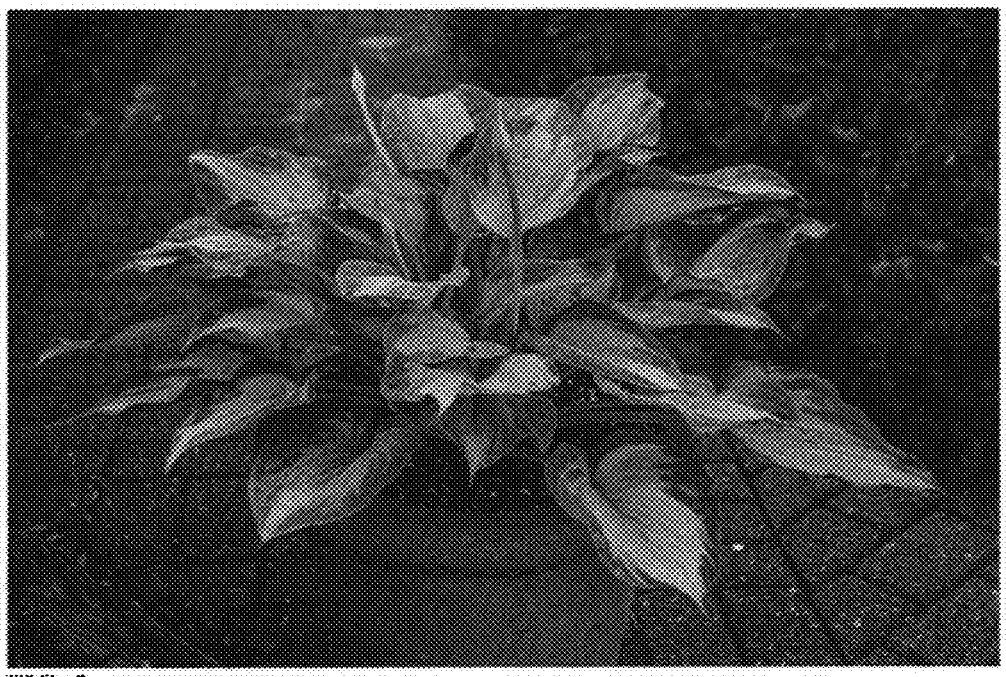
FIG. 2 shows a semi-mature plant in a container with early scapes.
Figure 3:
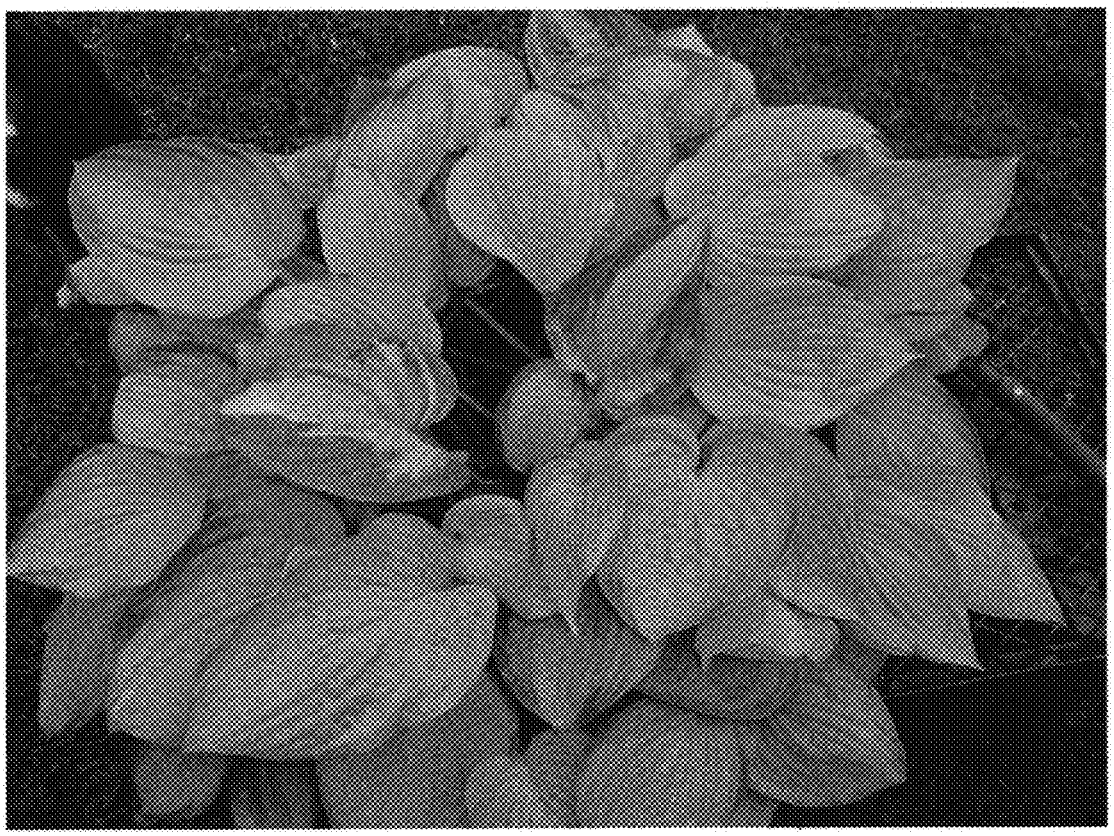
FIG. 3 shows the original single division sport mutation with wider margins in the nursery flat of 'Step Sister'.

The following descriptions and color references are based on the 2015 edition of The Royal Horticultural Society Colour Chart except where common dictionary terms are used. The new plant, *Hosta* 'Sister Act', has not been observed under all possible environmental conditions. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a ten-year-old plant in a shaded trial garden in Indianapolis, Ind. provided supplemental water and fertilizer.

Botanical classification: *Hosta* x hybrid;

Parentage: Sport mutation of 'Step Sister';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Typically between RHS 155D and RHS NN155C when actively growing depending on soil mineralization;

Plant shape and habit: Hardy herbaceous perennial with a basal rosette of leaves and petioles emerging from rhizomes producing a low spreading mound with slightly arching scapes flowering just above foliage;

Plant size: Foliage height to about 50.8 cm above soil line to the top of the leaves, and to about 101.6 cm wide at the widest point slightly above the soil line;

Foliage description: Ovate; acute apex, cordate base, entire margin; glabrous both surfaces; lightly glaucous adaxial and strongly glaucous abaxial; blades stiff; with slight dimpling and corrugation; moderately impressed adaxial veins and costate abaxial veins;

Leaf blade size: To about 28.0 cm long and about 22.9 cm wide; average about 26.5 cm long and 21.0 cm wide; margin variable in an individual leaf and increasing with maturity from 1.5 cm to about 7.6 cm wide; center variable in an individual leaf and decreasing with maturity from 15.0 cm to 8.0 cm;

Leaf blade color: Early season and expanding adaxial margin nearest RHS 137A and abaxial margin nearest RHS 137B, adaxial center nearest RHS 146D and abaxial center nearest RHS 146D, adaxial and abaxial intermediate colors not apparent; mid-season and mature adaxial margins between RHS 137B and RHS 137A, abaxial margin between RHS 137B and RHS 191A, adaxial center between RHS 11C and RHS 160C, abaxial center between RHS 11D and RHS 160D, adaxial intermediate color nearest RHS N144A, abaxial intermediate color between RHS 145A and RHS 146D;

Petiole: Hlabrous and slightly glaucous both adaxial and abaxial; deeply "V" shaped; stiff; to 40.6 cm long and 14.0 mm wide at base and about 10.0 mm deep near base, average about 38.0 cm long and 13.0 mm wide;

Petiole color: Distal adaxial margin about 12.0 mm wide nearest RHS 137A narrowing to 0.8 mm wide proximally and nearest RHS 146A; distal center between RHS 11C and RHS 146D, proximal center nearest RHS 146C; distal abaxial margins nearest RHS 146A and proximal margins nearest RHS 146C; abaxial midrib nearest RHS 145C, distal abaxial center RHS 145A proximal center between RHS 146D and 145A;

Veins: Thirteen to fourteen pairs with midrib; parallel; moderately impressed adaxial; costate and smooth abaxial;

Veins color: Adaxial margins nearest RHS 193A and centers between RHS 193A and RHS 145C; abaxial nearest RHS 193A;

Flower description:

Buds one to two days prior to opening: Clavate with rounded apex and narrow tube base; about 4 cm long and 1 cm in diameter at widest bulb portion, with base narrowing in basal 1.5 cm to about 0.3 cm diameter;

Bud color: Nearest RHS NN155D distally and nearest RHS NN155C with slight blush of nearest RHS 92D proximally;

Flowers: Perfect; campanulate; slightly drooping; to 4.4 cm long to exserted stigma; corolla fused in basal 3.0 cm, free in the distal 2.4 cm, about 1.5 cm wide at tepal apices, decreasing distally; corolla tube portion 1.8 cm long and 0.3 cm diameter; effective for a normal period, usually about one day on plant; flowers tightly arranged on scape; persistent after opening;

Flowering period: Scapes remain effective with flowers beginning late June for about four weeks;

Inflorescence: With about 40 flowers per scape; flowering in upper 18 cm; mostly secund;

Fragrance: No detectable fragrance;

Tepal: Two nearly identical sets of three, glabrous; entire margins;

*Inner set*.—About 4.0 cm long and 8.0 mm wide slightly above fusion point; fused in basal 3.0 cm; clavate with acute apex; entire margin; basal 1.8 cm fused into tube.

*Inner set color*.—Adaxial and abaxial nearest RHS NN155D with adaxial having very lightly blushed nearest RHS 91D; corolla tube base adaxial and abaxial nearest RHS 91D.

*Inner set*.—About 4.0 cm long and 8.0 mm wide slightly above fusion point; fused in basal 3.0 cm; clavate with acute apex; entire margin; basal 1.8 cm fused into tube.

*Inner set color*.—Adaxial and abaxial nearest RHS NN155D with adaxial having very lightly blushed nearest RHS 91D; corolla tube base adaxial and abaxial nearest RHS 91D.

Gynoecium: Single; 4.4 cm long; superior;

*Style*.—Cylindrical; about 3.8 cm long, 0.2 cm diameter; arcuate upward 90 degrees in distal 10.0 mm; color nearest RHS NN155D distally and nearest RHS 145D proximally.

*Stigma*.—Puberulent; tri-lobed; about 1.2 mm across and 1.0 mm tall; color nearest RHS NN155A.

*Ovary*.—Ellipsoidal; superior; apex rounded; base rounded to truncate; to about 6 mm long and 3 mm diameter in middle; color nearest RHS 145A.

Androecium: Six;

*Filaments*.—Six, approximately 4.0 cm long and 0.2 cm in diameter; curved upward to nearly 90 degrees in the distal 5.0 mm; color distally nearest RHS NN155B, base nearest RHS 145D.

*Anthers*.—Ellipsoidal with rounded ends; dorsifixed; longitudinal; about 3.5 mm long and 1.2 mm wide; color nearest RHS 164C.

*Pollen*.—Spherical; less than 0.1 mm long; color nearest RHS 17B.

Peduncle: Cylindrical; usually one per mature division; about 10 per plant; glabrous; glaucous; mostly erect with small arching distally; to about 90 cm tall, and about 1.0 cm in diameter at base, average about 88 cm tall and 0.9 cm diameter at base;

Inflorescence: Flowering in distal one-third of peduncle; with small floral bracts subtending each flower;

Peduncle color: Proximal portion below leaves between RHS N138D and RHS 191C, distal portion nearest RHS N138B;

Pedicel: Terete; glabrous; slightly lustrous; about 11.0 mm long and 1.5 mm diameter decreasing distally; slightly drooping;

Pedicel color: Nearest RHS 138B;

Floral bracts: Each flower normally subtended by a single bract; lanceolate; narrowly acute apex and truncate base; entire margin; glabrous and glaucous abaxial and adaxial; to about 4.5 cm long and 1.0 cm wide, decreasing distally; forming upright beak prior to bud development; drying after flowers open;

Fruit and seed: Not yet observed;

Disease resistance: The new plant shows some resistance to slug feeding. Other resistance or susceptibility to pests (including: *Odocoileus virginianus* and *Oryctotagus cuniculus*) and diseases common to *Hostas* has not been observed. The plant grows best and shows best coloration with good drainage, plenty of water, light cool shade, but is able to tolerate some drought when mature. Hardiness at least from USDA zone 3 through 8, and other disease resistance is typical of that of other *Hostas*.

It is claimed:

1. A new and distinct *Hosta* plant cultivar named *Hosta* 'Sister Act' as herein described and illustrated.

* * * * *